United States Patent [19]

McCaulay

[11] 4,144,282

[45] Mar. 13, 1979

[54] OCTANE UPGRADING OF LIGHT NAPHTHA STREAMS USING A FLUOROSULFONIC ACID, HYDROFLUORIC ACID AND ANTIMONY PENTAFLUORIDE CATALYST

[75] Inventor: David A. McCaulay, Homewood, Ill.

[73] Assignee: Standard Oil Company (Indiana), Chicago, Ill.

[21] Appl. No.: 571,737

[22] Filed: Apr. 25, 1975

Related U.S. Application Data

[63] Continuation-in-part of Ser. No. 385,596, Aug. 3, 1973, abandoned.

[51] Int. Cl.² .......................... C07C 5/28; B01J 27/12
[52] U.S. Cl. ................................ 260/683.68; 252/441
[58] Field of Search ................... 260/683.68; 252/441

[56] References Cited

U.S. PATENT DOCUMENTS 3,766,286  10/1973  Olah ............................... 260/683.68

FOREIGN PATENT DOCUMENTS 742746  9/1966  Canada ............................... 260/683.68

Primary Examiner—George Crasanakis
Attorney, Agent, or Firm—Reed F. Filey; Arthur G. Gilkes; William T. McClain

[57] ABSTRACT

Catalyst and process for octane upgrading of a light naphtha feed using fluorosulfonic acid and antimony pentafluoride to which a small amount of hydrogen fluoride is added. The catalyst is at least as active as the fluorosulfonic acid-antimony pentafluoride system and in addition shows enormously improved selectivity and lifetime.

14 Claims, 3 Drawing Figures

OCTANE UPGRADING OF LIGHT NAPHTHA STREAMS USING A FLUOROSULFONIC ACID, HYDROFLUORIC ACID AND ANTIMONY PENTAFLUORIDE CATALYST

RELATED APPLICATIONS

This application is a continuation-in-part of copending application Ser. No. 385,596 filed Aug. 3, 1973 and now abandoned.

SUMMARY OF THE INVENTION

This invention relates to a novel catalyst and process for converting a light naphtha feed into a mixture of higher octane hydrocarbons and, more particularly, it relates to an improved fluorosulfonic acid-antimony pentafluoride catalyst for the conversion of pentanes, hexanes or mixtures thereof and its use in processes for the octane upgrading of light naphtha feeds.

In accordance with the instant invention, a light naphtha feed composed primarily of pentanes, hexanes or mixtures thereof is contacted, preferably after desulfurization, drying and dearomatizing of the feed to improve catalyst lifetime, in either a continuous or a batch type process at about ambient temperature or below with an fluorosulfonic acid-antimony pentafluoride mixture containing a few percent of hydrogen fluoride to convert said feed into product containing a mixture of hydrocarbons having a substantially higher octane number. The ternary mixture is at least as active as the fluorosulfonic acid-antimony pentafluoride catalyst system and in addition can show enormously improved selectivity and lifetime.

BACKGROUND OF THE INVENTION

Light naphtha stream conversion to higher octane mixtures is an important part of the oil refining process and has been accomplished by a number of different catalysts in the past including such combinations as mixtures of hydrogen fluoride and antimony pentafluoride and mixtures of fluorosulfonic acid and antimony pentafluoride. The latter mixtures are called "super acid" catalysts in the art. However, for octane upgrading, $HF-SbF_5$ mixtures are of only moderate activity and selectivity while $FSO_3H-SbF_5$ mixtures, although having substantially better activities, have a relatively short catalyst lifetime in that cracking and other adverse side reactions set in after a short time on stream.

An example of the use of hydrogen fluoride-antimony pentafluoride mixtures is set out in Canadian Patent No. 742,746 in which use of $HSbF_6$ and its mixtures with hydrogen fluoride are taught and an example of the use of fluorosulfonic acid-antimony pentafluoride mixtures is set forth in U.S. Pat. No. 3,766,286.

Now it has been found that by combining a fluorosulfonic acid-antimony pentafluoride catalyst with a small amount of hydrogen fluoride a far more selective conversion catalyst having an activity about the same as fluorosulfonic acid based catalysts is produced which has enormously improved catalyst lifetime as the hydrogen fluoride acts as a suppressor of unwanted side reactions. Thus, the usual octane upgrading processes such as isomerization which occur when the catalyst of the instant invention is in contact with hydrocarbons under the appropriate temperature, pressure and concentration conditions are effected with a substantially higher efficiency than has been heretofore obtained and considerable economic savings are obtained by the lowered amount of cracking and longer catalyst lifetime.

STATEMENT OF THE INVENTION

Figure 1:
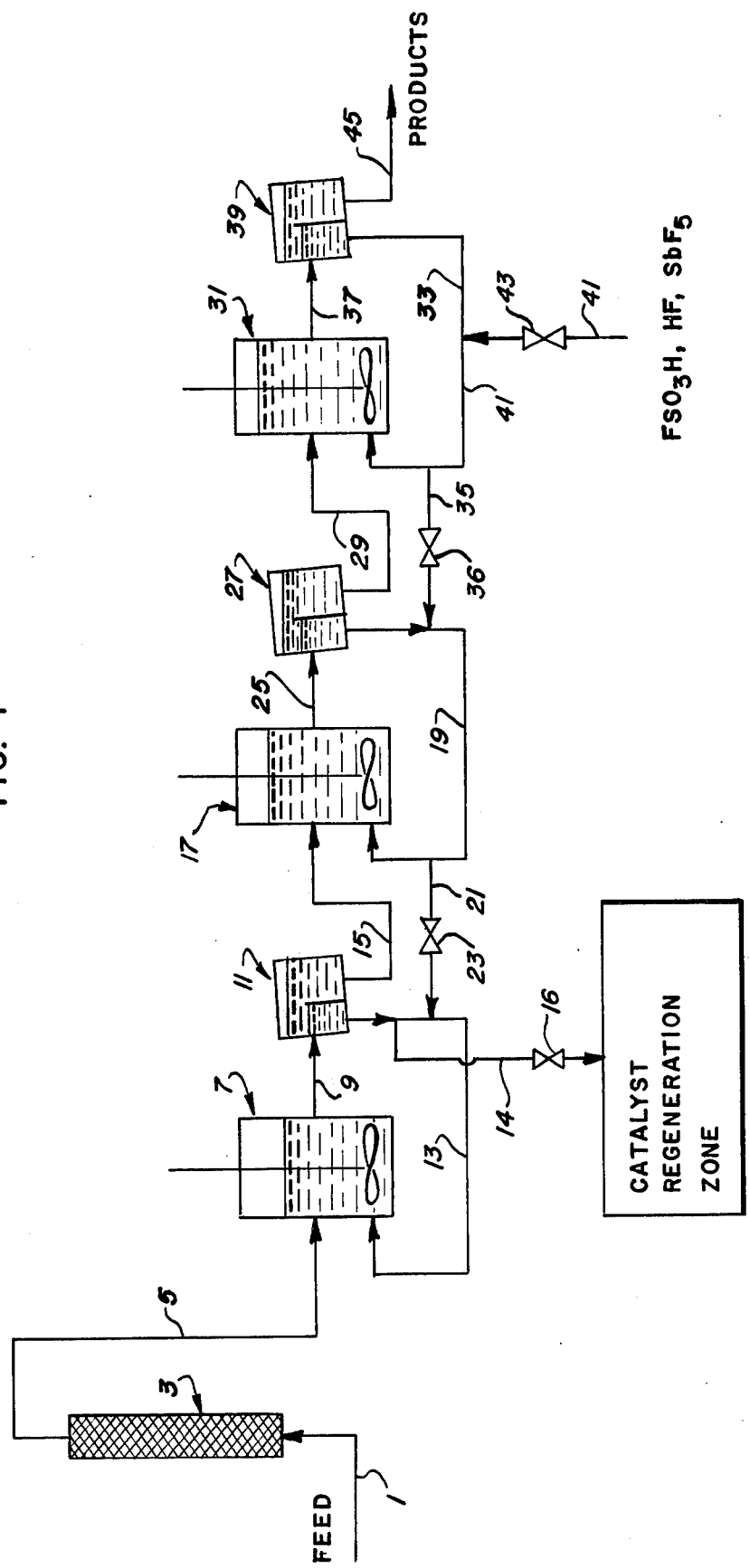
FIG. 1 shows one embodiment of a continuous process using the instant invention whereby a light naphtha feed is converted into a higher octane hydrocarbon mixture and a slipstream of conversion catalyst is continually removed and catalyst replenished.
Figure 2:
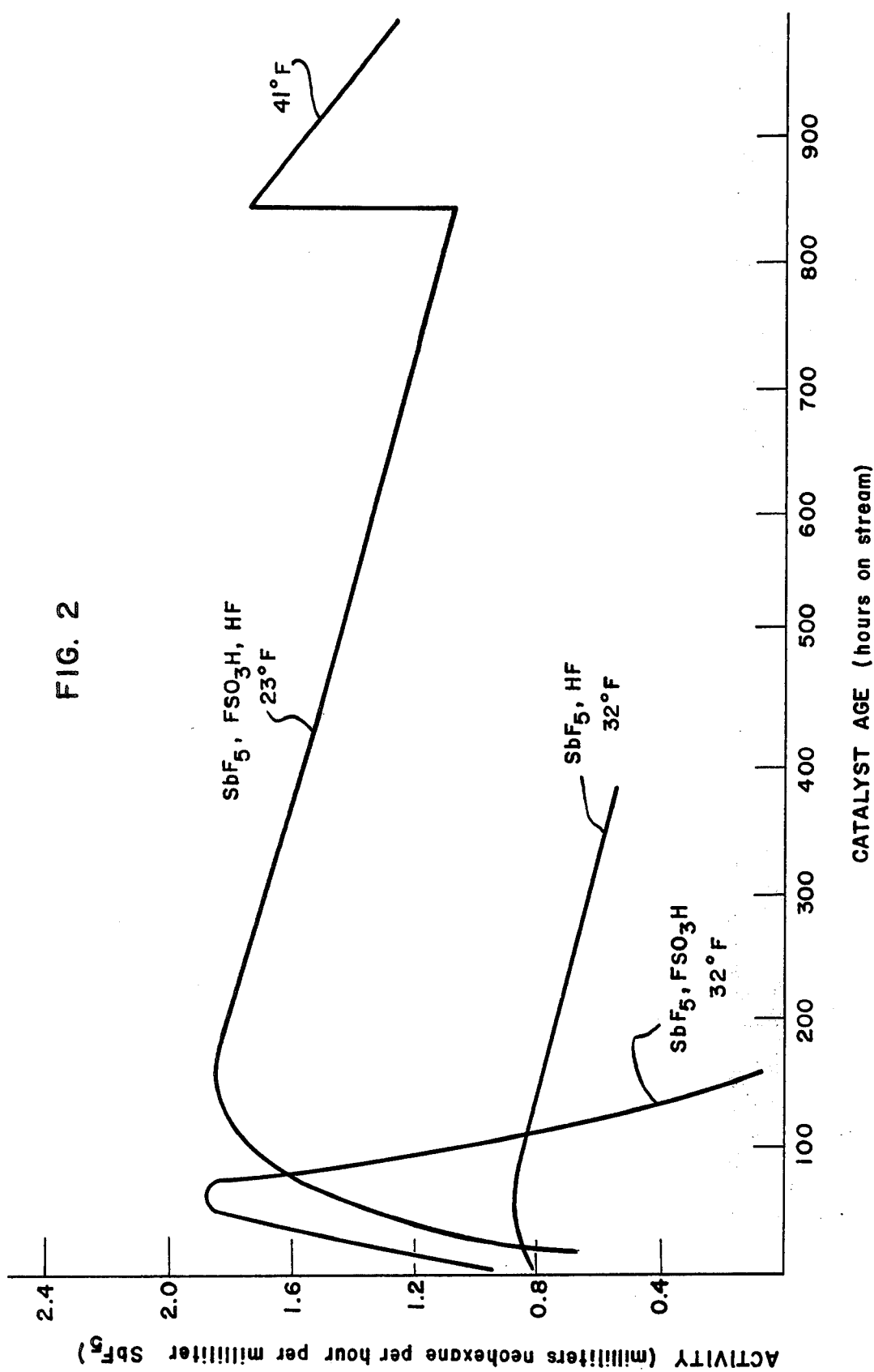
FIG. 2 which is a plot of Examples I, III and IV shows comparative activities expressed as milliliters neohexane per milliliter of $SbF_5$ per hour of the catalyst of the instant invention and catalysts composed of hydrogen fluoride and fluorosulfonic acid, each in combination with antimony pentafluoride, using a feed of 2-methylpentane.
Figure 3:
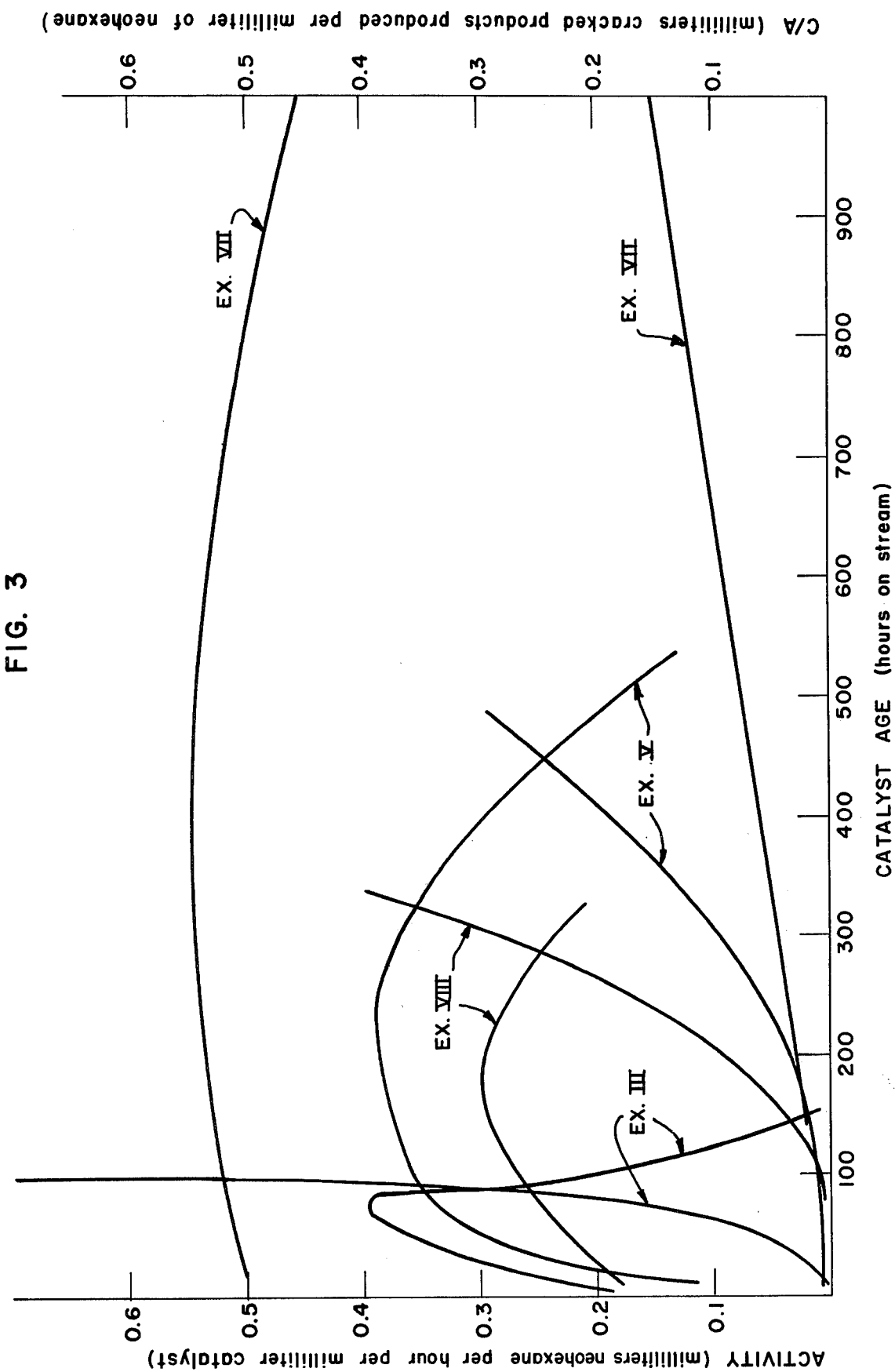
FIG. 3 which is a plot of Examples III, V, VII and VIII shows comparative activities and cracking to activity ratios, C/A, for two catalysts of the instant inventions (at different concentration ratios), the fluorosulfonic acid-antimony pentafluoride catalyst and the hydrogen fluoride-antimony pentafluoride catalyst. Activities in FIG. 3 are calculated on the basis of the total volume of catalyst used.

In one embodiment of the process, as illustrated in FIG. 1, a light naphtha feed, preferably dried and desulfurized, comprised of pentanes, hexanes or mixtures thereof is passed through line 1 into dearomatizer 3 (preferably, dearomatization may be accomplished by catalytic hydrogenation or by adsorption on 13X molecular sieves) and then through line 5 into reactor 7 which is preferably equipped for vigorous agitation of the contents. The feed usefully contains at least some and, more preferably, about 2 to about 30 weight percent and, most preferably, about 5 to about 20 weight percent methylcyclopentane or cyclohexane or another inhibitor to prevent "run-away" cracking. "Run-away" cracking here probably involves the production of isobutane and a highly unsaturated material, "red-oil," and its inhibition is well-known in the art. The production of a small amount of this basic "red-oil" during conversion is primarily responsible for the destruction of the catalyst activity and its formation requires make-up catalyst to be constantly added and catalyst to be continuously removed, both in small amounts, in a continuous process.

In reactor 7, the feed is intimately contacted with catalyst entering via line 13. Reactor 7 temperature is preferably kept between about 10° C. and about 30° C. and, more preferably, between about 15° C. and about 25° C.

Make-up or start-up catalyst entering through line 41 consists preferably of a mixture of about 0.1 to about 3 volumes, more preferably, about 0.4 to about 1.6 volumes and, most preferably, about 0.6 to about 1.2 volumes of antimony pentafluoride per volume of fluorosulfonic acid. This mixture additionally contains preferably about 2 to about 20, more preferably, about 3 to about 15 and, most preferably, about 5 to about 10 weight percent of hydrogen fluoride based upon the amount of fluorosulfonic acid used. Alternatively, the three components of the catalyst may be introduced separately into the reactor or catalyst recycle-line and combined by the agitation in the reactor.

Space velocities are important in a continuous process using the instant invention and they depend upon the amount of octane upgrading desired, the reactor temperature and the catalyst age. A lower space velocity will of course be used at a lower reaction temperature or if higher conversion efficiencies are desired using fewer reactors. For the usual octane upgrading with an equilibrium concentration catalyst it has been found that at about 16° C. space velocities between about 1.6 to about 4.0 volumes of feed per volume of antimony pentafluoride per hour are useful. At about −5° C., a space velocity between about 0.05 to about 0.13 volumes of feed per volume of antimony pentafluoride per hour is used and at about 0° C., the space velocity is usefully about 0.8 to about 2.0 volumes of feed per volume of antimony pentafluoride per hour. However, the proper space velocities to be used will be evident to one skilled in this art.

The reactor effluent from reactor 7 is passed through line 9 into settler 11 where the heavier catalyst phase separates as a bottom layer and is recycled to reactor 7 via line 13. A controlled slipstream of catalyst is removed via line 14 to the catalyst regeneration zone through valve 16 where "red-oil" and associated products are removed from the catalyst components. These components, if economically feasible, may be converted back into catalyst which can then be reused. The upper hydrocarbon phase is removed from settler 11 through line 15 into a second reactor 17 which is preferably equipped for agitation.

In reactor 17, the feed is intimately contacted again with catalyst entering via line 19. Reactor 17 temperature can be kept at about the same as reactor 7 or, preferably, operated below the temperature of reactor 7. If held below, preferably, reactor 17 is held at a temperature in the range about 0° C. to about 20° C. and, more preferably, about 5° C. to about 15° C. Line 21 which connects lines 19 and 13 is designed to provide a controlled slipstream of catalyst from line 19 into line 13, the size of which is adjustable by valve 23, and serves to provide a slow flow of catalyst back to reactor 7 and to the regeneration zone from reactor 17.

The reactor effluent from reactor 7 is passed through line 25 into settler 27 where the heavier catalyst phase separates as a bottom layer and is recycled to reactor 17 via line 19. The upper hydrocarbon phase is removed from settler 27 through line 29 into a third reactor 31 which is preferably equipped for agitation.

In reactor 31, the feed is intimately contacted again with catalyst entering via line 33. A controlled slipstream of catalyst which takes catalyst back into line 19 is provided by line 35 and valve 36. Reactor 31 can be operated at about the same temperature as either or both of the two preceding reactors or, more preferably, its temperature kept below their temperatures. If held below, preferably, reactor 31 is held at a temperature in the range about −10° C. to about 10° C. and, more preferably, about −5° C. to about 5° C.

The reactor effluent from reactor 31 is fed into settler 39 via line 37 where the heavier catalyst phase separates as a bottom layer and is recycled to reactor 31 via line 33. Make-up catalyst is introduced in this embodiment via line 41 and can be controlled by valve 43. Hydrocarbon which is upgraded in its octane rating is removed through line 45 and may be put through one or more distillation stages to remove entrained catalyst and separate higher boiling hydrocarbon ends.

In the embodiment shown, three reactors in tandem are employed but it is obvious that by adjusting reactor temperature and space velocity, any number can be employed depending upon the octane upgrading desired and economic factors. In the mode shown in FIG. 1, wherein the feed meets catalyst at successively lower temperatures and maximum octane upgrading is desired, three reactors appear optimum. An advantage of the mode of FIG. 1 is that catalyst lifetime is enhanced by having the freshest catalyst meet feed already close to the equilibrium concentration of higher octane components at the lowest temperature used just prior to removing the product hydrocarbon from the process.

Alternatively, the reactors may be compressed into a single horizontal reactor containing two or more stages separated by weirs and each stage separately agitated. The temperature may be held constant or a gradient may be set up with the temperature decreasing towards the exit stream end.

While the invention is described in connection with the specific examples below, it is to be understood that these are for illustrative purposes only. Many alternatives, modifications and variations will be apparent to those skilled in the art in the light of the below Examples and such alternatives, modifications and variations fall within the scope and spirit of the appended claims.

GENERAL EXPERIMENTAL PROCEDURE

The antimony pentafluoride and fluorosulfonic acid were obtained from Allied Chemical Company, Special Chemicals Division, and the hydrogen fluoride from Matheson Gas Products. All were used without further purification except the fluorosulfonic acid, which was distilled at atmospheric pressure in an all-glass apparatus and a heart-cut boiling between 162°–164° C. collected and used. The hydrocarbons used were Phillips "Pure" grade and were percolated through silica-gel and 13X molecular sieves before use to remove remaining traces of water, olefins or aromatics.

The activity, A, of the catalyst was calculated from the concentration of neohexane (2,2-dimethylbutane) in the hexane fraction of each batch product, by means of the relation:

$$A = S \times \text{Neo}_{eq.} \times \ln\left(\frac{\text{Neo}_{eq.}}{\text{Neo}_{eq.} - \text{Neo}}\right) = (\text{at } 5° \text{ C.})$$

$$\frac{175 \times 0.62}{13 \times \text{batch contact time}} \ln\left(\frac{0.62}{0.62 - \text{Neo}}\right)$$

where, $$S = VHSV = \frac{\text{Volume of Hydrocarbon in Batch}}{(\text{volume of SbF}_5 \text{ in catalyst}) \times (\text{batch contact time, hours})}$$

Neo = Concentration of neohexane in batch product.
Neo$_{eq.}$ = Equilibrium concentration of neohexane, and, $$k_{-5°} = \frac{0.62}{\text{batch contact time}} \ln\left(\frac{0.62}{0.62 - \text{Neo}}\right)$$

Selectivity of the catalyst systems is measured by the cracking to activity ratio, C/A. C is determined by the relationship:

$$C = S \times \ln\left(\frac{1}{1-c}\right)$$

where c is the total concentration of the $C_1$ through $C_5$ products and A is the activity, A, as above.

The following Examples were carried out in a 300 milliliter, Hastelloy C, magnetically-driven stirred autoclave. The autoclave was first evacuated and the catalyst components added by displacement from Kel-F volume-meaasuring tubes. The autoclave was immersed in a refrigerated, constant temperature bath to keep it at the desired temperature. The hydrocarbon feed (2-methylpentane plus 14 percent methylcyclopentane) was added batchwise from a Ruska pump. The mixture was stirred for the desired length of time and then allowed to settle for about 15 minutes. The entire hydrocarbon layer was then withdrawn through a standpipe terminating in the reactor just above the acid-hydrocarbon interface. A new charge of feed was added to the same batch of catalyst and stirring was resumed. This procedure was repeated until the catalyst was no longer active. Samples of the hydrocarbon products were analyzed by gas chromatography.

EXAMPLE I

This Example was carried out at −5° C. using 36 milliliters (61.8) grams of fluorosulfonic acid, 5 milliliters (4.7 grams) of hydrogen fluoride, 13 milliliters (39.0 grams) of antimony pentafluoride. A 175 milliliter portion, 120.0 grams, of hydrocarbon was employed per batch.

TABLE I

| Batch Number | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Batch Contact Time, hours | | 18.0 | 6.68 | 140.5 | 116.0 | 7.12 | 16.17 | 7.08 | 16.0 | 7.20 | 16.0 | 7.27 | 15.9 | 23.6 | 23.2 | 71.7 |
| Total Time on Stream, hours | | 18.0 | 25.5 | 166 | 282 | 290 | 306 | 314 | 330 | 338 | 354 | 362 | 378 | 402 | 426 | 434 |
| Weight Catalyst Withdrawn in Product, grams | | 0.20 | 0.21 | 0.21 | 0.19 | 0.22 | 0.21 | 0.37 | 0.19 | 0.19 | 0.19 | 0.21 | 0.20 | 0.20 | 0.20 | 0.21 |
| Composition of Hydrocarbon, Weight Percent | Feed | | | | | | | | | | | | | | | |
| Propane | 0.0 | 0.0 | 0.0 | 0.0 | 0.0 | 0.1 | 0.0 | 0.1 | 0.0 | 0.1 | 0.0 | 0.1 | 0.0 | 0.1 | 0.2 | 0.2 | 0.0 |
| Isobutane | 0.0 | 0.0 | 0.0 | 0.0 | 0.3 | 1.6 | 0.5 | 1.1 | 0.9 | 2.1 | 1.0 | 1.8 | 1.1 | 2.4 | 2.9 | 2.9 | 1.1 |
| n-Butane | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Isopentane | 0.0 | 0.0 | 0.0 | 0.0 | 0.1 | 0.5 | 0.2 | 0.4 | 0.3 | 0.9 | 0.4 | 0.8 | 0.4 | 1.1 | 1.4 | 1.4 | 0.5 |
| n-Pentane | 0.0 | 0.0 | 0.0 | 0.0 | 0.0 | 0.0 | 0.0 | 0.0 | 0.0 | 0.1 | 0.0 | 0.1 | 0.0 | 0.1 | 0.1 | 0.1 | 0.0 |
| 2,2-Dimethylbutane | 0.0 | 44.1 | 30.9 | 56.0 | 54.0 | 40.3 | 49.9 | 40.5 | 50.2 | 40.5 | 50.0 | 40.0 | 50.3 | 50.7 | 50.7 | 36.1 |
| 2,3-Dimethylbutane | 2.8 | 9.7 | 12.5 | 6.9 | 6.5 | 9.8 | 7.1 | 9.4 | 6.8 | 4.3 | 6.8 | 9.1 | 6.7 | 6.4 | 6.4 | 10.7 |
| 2-Methylpentane | 81.8 | 22.5 | 28.0 | 16.6 | 15.6 | 22.2 | 16.6 | 21.6 | 15.8 | 21.5 | 16.7 | 21.4 | 15.7 | 14.7 | 14.7 | 23.6 |
| 3-Methylpentane | 0.9 | 9.2 | 11.6 | 6.7 | 6.1 | 9.1 | 6.8 | 8.8 | 6.5 | 9.0 | 6.7 | 8.8 | 6.3 | 6.0 | 6.0 | 9.5 |
| n-Hexane | 0.1 | 4.1 | 4.3 | 2.6 | 2.5 | 4.0 | 2.9 | 3.9 | 2.8 | 4.0 | 2.8 | 4.0 | 2.7 | 2.5 | 2.5 | 4.2 |
| Methylcyclopentane | 14.4 | 0.5 | 0.7 | 0.5 | 0.6 | 0.7 | 0.7 | 0.7 | 0.6 | 0.7 | 0.6 | 0.7 | 0.6 | 0.6 | 0.6 | 0.7 |
| Cyclohexane | 0.0 | 9.9 | 12.1 | 9.9 | 10.2 | 12.6 | 12.2 | 12.2 | 10.2 | 11.5 | 10.2 | 12.1 | 9.7 | 8.8 | 8.8 | 11.3 |
| Higher | 0.0 | 0.0 | 0.0 | 0.3 | 2.3 | 0.7 | 2.4 | 1.7 | 3.9 | 2.1 | 3.5 | 2.3 | 4.4 | 5.6 | 5.6 | 2.3 |
| Composition of Hexane Fraction, Weight Percent | Feed | | | | | | | | | | | | | | | |
| 2,2-Dimethylbutane | 0.0 | 49.2 | 35.4 | 63.0 | 63.8 | 47.6 | 59.9 | 48.1 | 61.2 | 48.1 | 60.3 | 47.9 | 61.6 | 63.2 | 63.2 | 42.9 |
| 2,3-Dimethylbutane | 3.3 | 10.8 | 11.3 | 7.8 | 7.6 | 11.6 | 8.5 | 11.2 | 8.3 | 11.1 | 8.2 | 11.0 | 8.2 | 8.0 | 8.0 | 12.7 |
| 2-Methylpentane | 95.5 | 25.1 | 32.1 | 18.7 | 18.4 | 26.2 | 20.0 | 25.6 | 19.2 | 25.5 | 20.1 | 25.7 | 19.3 | 18.3 | 18.3 | 28.1 |
| 3-Methylpentane | 1.1 | 10.3 | 13.2 | 7.5 | 7.2 | 10.7 | 8.1 | 10.5 | 7.9 | 10.7 | 8.1 | 10.5 | 7.7 | 7.5 | 7.5 | 11.3 |
| n-Hexane | 0.1 | 4.6 | 4.9 | 3.0 | 2.9 | 4.8 | 3.5 | 4.6 | 3.4 | 4.8 | 3.4 | 4.8 | 3.3 | 3.1 | 3.1 | 5.0 |
| $k_{-5}°$ | | 0.053 | 0.078 | | | 0.124 | 0.117 | 0.128 | | 0.126 | 0.124 | 0.124 | | | | 0.100 |
| A* | | 0.716 | 1.05 | | | 1.67 | 1.58 | 1.73 | | 1.69 | 1.67 | 1.67 | | | | 1.35 |

TABLE II

| Batch Number | 20 | 25 | 30 | 35 | 40 | 45** | 46 | 47 | 48 | 49 | 50 | 55 | 60 | 65 |
|---|---|---|---|---|---|---|---|---|---|---|---|---|---|---|
| Batch Number Time, hours | 16.07 | 22.25 | 16.05 | 7.20 | 16.18 | 7.30 | 16.03 | 7.12 | 17.36 | 25.42 | 20.47 | 7.38 | 19.08 | 7.08 |
| Total Time on Stream, hours | 498 | 571 | 642 | 698 | 786 | 842 | 858 | 866 | 883 | 909 | 930 | 986 | 1053 | 1130 |
| Weight Catalyst Withdrawn in Product, grams | 0.15 | 0.17 | 0.31 | 0.17 | 0.20 | 0.25 | 0.21 | 0.25 | 0.24 | 0.24 | 0.25 | 0.33 | 0.25 | 0.64 |
| Composition of Hydrocarbon, Weight Percent | | | | | | | | | | | | | | |
| Propane | 0.1 | 0.2 | 0.1* | 0.0 | 0.1 | 0.1 | 0.3 | 0.1 | 0.3 | 0.4 | 0.3 | 0.1 | 0.2 | 0.0 |
| Isobutane | 2.7 | 2.8 | 2.7 | 1.6 | 2.5 | 2.4 | 3.4 | 2.2 | 3.5 | 4.0 | 3.9 | 1.6 | 2.7 | 1.0 |
| n-Butane | 0.0 | 0.0 | 0.0 | 0.0 | 0.0 | 0.0 | 0.0 | 0.0 | 0.0 | 0.0 | 0.0 | 0.0 | 0.0 | 0.0 |
| Isopentane | 1.3 | 1.3 | 1.3 | 0.7 | 1.1 | 1.1 | 1.7 | 1.0 | 1.7 | 2.4 | 2.2 | 0.7 | 1.3 | 0.5 |
| n-Pentane | 0.1 | 0.1 | 0.1 | 0.0 | 0.1 | 0.1 | 0.2 | 0.1 | 0.2 | 0.3 | 0.3 | 0.0 | 0.1 | 0.0 |
| 2,2-Dimethylbutane | 47.8 | 49.2 | 46.7 | 30.4 | 47.4 | 38.4 | 45.0 | 38.3 | 45.9 | 44.3 | 44.9 | 34.2 | 45.8 | 25.7 |
| 2,3-Dimethylbutane | 7.1 | 6.9 | 7.4 | 10.9 | 6.4 | 8.9 | 6.6 | 9.1 | 6.8 | 6.4 | 6.6 | 10.2 | 7.7 | 12.8 |
| 2-Methylpentane | 15.9 | 15.0 | 16.6 | 23.3 | 17.1 | 20.3 | 15.2 | 20.5 | 15.8 | 15.1 | 15.5 | 23.5 | 17.1 | 28.2 |
| 3-Methylpentane | 6.3 | 6.1 | 6.9 | 10.0 | 6.9 | 8.7 | 6.6 | 8.9 | 6.7 | 6.5 | 6.6 | 10.0 | 7.3 | 12.1 |
| n-Hexane | 2.9 | 2.7 | 3.1 | 4.5 | 3.1 | 4.3 | 3.0 | 4.4 | 3.0 | 2.9 | 3.0 | 4.8 | 3.5 | 4.7 |
| Methylcyclopentane | 0.6 | 0.6 | 0.6 | 0.7 | 0.7 | 0.8 | 0.7 | 0.8 | 0.7 | 0.6 | 0.6 | 0.9 | 0.9 | 1.1 |
| Cyclohexane | 9.5 | 9.3 | 9.5 | 11.4 | 4.3 | 9.8 | 7.7 | 10.4 | 8.0 | 6.6 | 7.2 | 11.1 | 8.7 | 11.8 |
| Higher | 5.6 | 5.8 | 5.1 | 2.9 | 5.4 | 5.2 | 9.8 | 4.4 | 7.2 | 10.6 | 8.9 | 3.0 | 4.8 | 2.1 |
| Composition of Hexane Fraction, Weight Percent | | | | | | | | | | | | | | |
| 2,2-Dimethylbutane | 59.7 | 61.5 | 57.9 | 41.1 | 55.6 | 47.7 | 59.0 | 47.2 | 58.6 | 59.0 | 58.6 | 41.4 | 56.3 | 30.8 |
| 2,3-Dimethylbutane | 8.8 | 8.6 | 9.1 | 13.2 | 7.9 | 11.1 | 8.6 | 11.2 | 8.7 | 8.5 | 8.7 | 12.3 | 9.4 | 15.3 |
| 2-Methylpentane | 19.9 | 18.8 | 20.7 | 28.2 | 21.2 | 25.2 | 19.9 | 25.2 | 20.2 | 20.1 | 20.2 | 28.4 | 21.1 | 13.8 |
| 3-Methylpentane | 7.9 | 17.7 | 8.5 | 12.1 | 8.5 | 10.8 | 8.6 | 10.9 | 8.6 | 8.6 | 8.7 | 12.0 | 8.9 | 14.5 |
| n-Hexane | 3.7 | 3.4 | 3.8 | 5.4 | 3.9 | 5.3 | 3.9 | 5.4 | 3.9 | 3.9 | 3.9 | 5.8 | 4.3 | 5.7 |
| $k_{-5}°$ | 0.116 | 0.017 | 0.099 | 0.093 | 0.013 | | | | | | | | | |
| $k_{+5}°$ | | | | | | 0.127 | 0.129 | 0.128 | 0.114 | 0.082 | 0.097 | 0.094 | 0.082 | 0.061 |

TABLE II-continued

| Batch Number | 20 | 25 | 30 | 35 | 40 | 45** | 46 | 47 | 48 | 49 | 50 | 55 | 60 | 65 |
|---|---|---|---|---|---|---|---|---|---|---|---|---|---|---|
| A*** | 1.56 | 1.43 | 1.33 | 1.25 | 1.39 | 1.71 | 1.74 | 1.72 | 1.53 | 1.10 | 1.30 | 1.26 | 1.10 | 0.82 |

*A 6.2 gram portion of FSO₃H-HF added at batch 27.
**Temperature raised to about 5° C.
***Milliliters of neohexane per milliliter of antimony pentafluoride.

EXAMPLE II

This Example was carried out at 0° C. using the same amounts and procedure as Example I. The Example was terminated early because of a failure of the refrigeration system.

EXAMPLE III

This comparative Example was carried out at 0° C. using, instead of the catalyst of the instant invention, a comparison catalyst composed of 51 milliliters of fluorosulfonic acid and 13 milliliters of antimony pentafluoride. A 175 milliliter portion of hydrocarbon feed was used per batch.

TABLE III

| Batch Number | Feed | 1 | 2 | 3 | 4 | 5 | 6 | 7 | 8 |
|---|---|---|---|---|---|---|---|---|---|
| Batch Contact Time, Hours | | 16.5 | 6.7 | 16.25 | 7.43 | 16.05 | 7.24 | 16.55 | 6.34 |
| Total Time on Stream, Hours | | 16.5 | 24.0 | 40.5 | 48.0 | 64.0 | 72.0 | 88.0 | 96.0 |
| Composition of Hydrocarbon, Weight Percent | | | | | | | | | |
| Propane | 0.0 | 0.0 | 0.0 | 0.0 | 0.0 | 0.0 | 0.0 | 0.0 | 0.0 |
| Isobutane | 0.0 | 0.0 | 0.0 | 0.0 | 0.0 | 0.0 | 0.0 | 0.1 | 0.0 |
| n-Butane | 0.0 | 0.0 | 0.0 | 0.0 | 0.0 | 0.0 | 0.0 | 0.0 | 0.0 |
| Isopentane | 0.0 | 0.0 | 0.0 | 0.0 | 0.0 | 0.0 | 0.0 | 0.0 | 0.0 |
| n-Pentane | 0.0 | 0.0 | 0.0 | 0.0 | 0.0 | 0.0 | 0.0 | 0.0 | 0.0 |
| 2,2-Dimethylbutane | 0.0 | 48.1 | 36.3 | 52.2 | 43.4 | 52.9 | 42.4 | 52.7 | 40.9 |
| 2,3-Dimethylbutane | 2.8 | 8.5 | 10.4 | 7.2 | 9.2 | 7.3 | 9.3 | 7.2 | 9.2 |
| 2-Methylpentane | 81.8 | 21.2 | 24.9 | 17.7 | 21.2 | 16.8 | 21.4 | 16.7 | 22.4 |
| 3-Methylpentane | 0.9 | 8.5 | 10.3 | 7.1 | 8.5 | 6.8 | 8.9 | 6.9 | 9.3 |
| n-Hexane | 0.1 | 3.8 | 4.5 | 3.1 | 4.0 | 2.9 | 4.0 | 2.9 | 4.2 |
| Methylcyclopentane | 14.4 | 0.6 | 0.7 | 0.7 | 0.8 | 0.7 | 0.8 | 0.8 | 0.8 |
| Cyclohexane | 0.0 | 9.3 | 12.9 | 12.0 | 13.0 | 12.5 | 13.2 | 12.7 | 13.2 |
| Higher | 0.0 | 0.0 | 0.0 | 0.0 | 0.0 | 0.0 | 0.1 | 0.1 | 0.0 |
| Composition of Hexane Fraction, Weight Percent | | | | | | | | | |
| 2,2-Dimethylbutane | 0.0 | 53.4 | 42.0 | 59.8 | 50.3 | 61.0 | 49.4 | 61.0 | 47.5 |
| 2,3-Dimethylbutane | 3.3 | 9.4 | 12.1 | 8.3 | 10.6 | 8.5 | 10.8 | 8.3 | 10.7 |
| 2-Methylpentane | 95.5 | 23.5 | 28.8 | 20.2 | 24.5 | 19.4 | 24.9 | 19.3 | 26.1 |
| 3-Methylpentane | 1.1 | 9.5 | 11.9 | 8.2 | 9.9 | 7.8 | 10.3 | 8.0 | 10.8 |
| n-Hexane | 0.1 | 4.2 | 5.2 | 3.5 | 4.6 | 3.3 | 4.6 | 3.4 | 4.9 |
| $k_0$ | | 0.074 | 0.105 | 0.128 | 0.139 | 0.159 | 0.136 | 0.156 | 0.142 |
| A* | | 1.00 | 1.41 | 1.71 | 1.88 | 2.15 | 1.83 | 2.10 | 1.92 |

*Milliliters of neohexane per milliliter of antimony pentafluoride.

TABLE IV

| Batch Number | Feed | 1 | 2 | 3 | 4 | 5 | 6 | 7 | 8 | 9 | 10 | 11 | 12 |
|---|---|---|---|---|---|---|---|---|---|---|---|---|---|
| Time on Stream, Hours | | 5.9 | 26.0 | 49.7 | 70.2 | 77.5 | 93.9 | 100.9 | 117.2 | 124.4 | 140.8 | 148.1 | 164.5 |
| Batch Continued, Hours | | 5.9 | 20.1 | 23.7 | 20.6 | 7.3 | 16.4 | 7.4 | 16.3 | 7.3 | 16.4 | 7.3 | 16.4 |
| Composition of Product, Weight Percent | | | | | | | | | | | | | |
| Propane | 0.0 | 0.0 | 0.0 | 0.1 | 0.2 | 0.1 | 0.0 | 0.0 | 0.0 | 0.0 | 0.0 | 0.0 | 0.0 |
| Isobutane | 0.0 | 0.0 | 0.4 | 2.7 | 4.1 | 2.3 | 3.6 | 2.2 | 3.9 | 1.2 | 2.4 | 0.3 | 0.1 |
| n-Butane | 0.0 | 0.0 | 0.0 | 0.0 | 0.0 | 0.0 | 0.0 | 0.0 | 0.0 | 0.0 | 0.0 | 0.0 | 0.0 |
| Isopentane | 0.0 | 0.0 | 0.2 | 1.6 | 2.3 | 1.2 | 2.4 | 1.2 | 2.6 | 0.7 | 1.5 | 0.3 | 0.0 |
| n-Pentane | 0.0 | 0.0 | 0.0 | 0.2 | 0.3 | 0.1 | 0.2 | 0.1 | 0.2 | 0.0 | 0.0 | 0.0 | 0.0 |
| 2,2-Dimethylbutane | 0.0 | 27.0 | 51.3 | 48.9 | 47.0 | 34.0 | 44.0 | 27.9 | 36.2 | 17.6 | 24.6 | 2.3 | 0.2 |
| 2,3-Dimethylbutane | 0.0 | 13.5 | 7.5 | 6.7 | 6.4 | 10.1 | 6.8 | 11.5 | 8.2 | 14.2 | 11.9 | 18.0 | 7.2 |
| 2-Methylpentane | 83.2 | 29.9 | 16.3 | 14.4 | 13.9 | 22.2 | 16.0 | 25.4 | 18.5 | 33.3 | 27.5 | 43.6 | 53.9 |
| 3-Methylpentane | 0.5 | 12.5 | 7.1 | 6.2 | 6.0 | 9.6 | 6.4 | 10.8 | 7.8 | 13.7 | 11.5 | 19.0 | 23.5 |
| n-Hexane | 0.0 | 4.6 | 3.2 | 2.7 | 2.7 | 4.5 | 2.9 | 4.6 | 4.0 | 3.7 | 4.3 | 0.8 | 0.2 |
| Methylcyclopentane | 16.3 | 0.9 | 0.8 | 0.7 | 0.6 | 0.7 | 0.5 | 0.7 | 0.6 | 0.7 | 0.5 | 0.9 | 8.1 |
| Cyclohexane | 0.0 | 11.9 | 12.0 | 8.4 | 7.1 | 10.3 | 6.9 | 10.4 | 7.5 | 11.2 | 9.5 | 12.8 | 6.0 |
| Heptanes and Higher | 0.0 | 0.0 | 1.3* | 8.0* | 9.4* | 5.1* | 10.3* | 5.2* | 10.5* | 3.6* | 6.4* | 2.0* | 0.8* |
| Hexane Isomer Ratios** | | | | | | | | | | | | | |
| 2-MP/3-MP | | 2.38 | 2.30 | 2.32 | 2.24 | 2.31 | 2.50 | 2.35 | 2.37 | 2.43 | 2.39 | 2.29 | 2.29 |
| 2,3-DMP/3-MP | | 1.08 | 1.06 | 1.08 | 1.03 | 1.05 | 1.06 | 1.06 | 1.05 | 1.04 | 1.03 | 0.95 | 0.31 |
| 2,2-DMP/3-MP | | 2.16 | 7.22 | 7.89 | 7.58 | 3.54 | 6.88 | 2.58 | 4.64 | 1.28 | 2.14 | 0.12 | 0.01 |
| n-Hexane/3-MP | | 0.37 | 0.45 | 0.44 | 0.45 | .47 | 0.45 | 0.43 | 0.51 | 0.27 | 0.37 | 0.05 | 0.01 |
| $k_0$ | | 0.072 | 0.102 | 0.117 | 0.140 | 0.097 | 0.099 | 0.069 | 0.057 | 0.036 | 0.026 | 0.004 | 0.0001 |
| A*** | 0.975 | 1.366 | 1.575 | 1.891 | 1.306 | 1.388 | 0.931 | 0.722 | 0.484 | 0.349 | 0.053 | 0.002 | |

TABLE IV-continued

| Batch Number | 1 | 2 | 3 | 4 | 5 | 6 | 7 | 8 | 9 | 10 | 11 | 12 |
|---|---|---|---|---|---|---|---|---|---|---|---|---|
| C/A | | | | | | | | | 0.074 | 0.093 | 0.224 | |

*Mainly $C_7$, $C_8$ and $C_9$ alkylcyclohexanes.
**MP is methylpentane and DMP is dimethylpentane.
***Milliliters of neohexane per milliliter of antimony pentafluoride.

EXAMPLE IV

This comparative Example was carried out at 0° C. using, instead of the catalyst of the instant invention, a comparison catalyst containing 13 milliliters (39 grams) of antimony pentafluoride and 52 milliliters (52 grams) of hydrogen fluoride. A 175 milliliter portion of 2-methylpentane feed was used per batch. Hydrogen gas at 25 p.s.i. was used in place of methylcyclopentane to inhibit run-away cracking.

TABLE V

| Batch Number | 1 | 2 | 3 | 4 | 5 | 10 | 15 | 20 | 25 | 30 |
|---|---|---|---|---|---|---|---|---|---|---|
| Time on Stream, Hours | 5.7 | 22.0 | 29.2 | 45.5 | 52.6 | 140.4 | 186.2 | 261.3 | 329.9 | 382.0 |
| Batch Contact Time, Hours | 5.7 | 16.3 | 7.2 | 16.3 | 7.1 | 16.5 | 16.3 | 27.5 | 16.4 | 4.9 |
| Composition of Product, Weight Percent | | | | | | | | | | |
| $C_1$-$C_2$ | 0.0 | 0.0 | 0.0 | 0.1 | 0.0 | 0.0 | 0.0 | 0.0 | 0.0 | 0.0 |
| Propane | 0.1 | 0.1 | 0.1 | 0.1 | 0.1 | 0.2 | 0.3 | 0.6 | 0.2 | 0.1 |
| Isobutane | 0.1 | 0.5 | 0.2 | 0.3 | 0.2 | 1.5 | 4.7 | 6.1 | 4.1 | 1.8 |
| n-Butane | 0.1 | 0.1 | 0.0 | 0.0 | 0.0 | 0.1 | 0.0 | 0.0 | 0.0 | 0.0 |
| Isopentane | 0.1 | 0.4 | 0.2 | 0.3 | 0.2 | 1.1 | 4.0 | 5.1 | 3.6 | 1.6 |
| n-Pentane | 0.0 | 0.0 | 0.0 | 0.0 | 0.0 | 0.1 | 0.4 | 0.6 | 0.3 | 0.1 |
| 2,2-Dimethylbutane | 26.3 | | 35.3 | | 33.2 | | 47.8 | 53.0 | 41.8 | 17.7 |
| 2,3-Dimethylbutane | 19.8 | | 15.2 | | 14.4 | | 8.5 | 7.1 | 10.7 | 19.5 |
| 2-Methylpentane | 31.6 | 98.9 | 27.9 | 99.2 | 30.9 | 96.8 | 21.9 | 16.8 | 24.2 | 35.9 |
| 3-Methylpentane | 15.8 | | 14.8 | | 14.7 | | 7.9 | 6.5 | 9.6 | 18.1 |
| n-Hexane | 6.2 | | 6.4 | | 6.4 | | 3.5 | 2.9 | 4.2 | 4.5 |
| Higher | 0.0 | 0.0 | 0.0 | 0.0 | 0.0 | 0.2 | 1.0 | 1.3 | 1.3 | 0.6 |
| $k_0$* | 0.060 | | 0.072 | | 0.067 | | 0.074 | Too Close to Equil. | 0.051 | 0.045 |
| A** | 0.811 | | 0.969 | | 0.896 | | 0.991 | | 0.689 | 0.609 |

*Where blank spaces occur values have not been tabulated.
**Mililiters of neohexane per milliliter of antimony pentafluoride.

EXAMPLE V

This Example was carried out using the amounts set out in EXAMPLE I except that 38 milliliters (65 grams) of fluorosulfonic acid and 2.2 milliliters (2.2 grams) of hydrogen fluoride were employed.

TABLE VI

| Batch Number | Feed | 1 | 2 | 3 | 4 | 5 | 6 | 7 | 8 | 9 |
|---|---|---|---|---|---|---|---|---|---|---|
| Batch Contact Time, hours | | 16 | 7.5 | 16 | 7 | 64.3 | 7.1 | 16.3 | 6.8 | 16.5 |
| Total Time on Stream, hours | | 16 | 24 | 40 | 47 | 112 | 120 | 136 | 144 | 160 |
| Composition of Hydrocarbon, Weight Percent* | | | | | | | | | | |
| Propane | 0 | 0 | 0 | 0 | 0 | 0.03 | 0 | 0 | 0 | 0 |
| Isobutane | 0 | 0.03 | 0.02 | 0.04 | 0.03 | 0.40 | 0.12 | 0.21 | 0.13 | 0.24 |
| n-Butane | 0 | 0.0 | 0 | 0 | 0 | 0 | 0 | 0 | 0 | 0 |
| Isopentane | 0 | 0.03 | 0 | 0 | 0 | 0.11 | 0.04 | 0.06 | 0.04 | 0.08 |
| n-Pentane | 0 | 0 | 0 | 0 | 0 | 0 | 0 | 0 | 0 | 0 |
| 2,2-Dimethylbutane | 0 | 34.74 | 26.80 | 50.01 | 35.44 | 55.36 | 58.44 | 50.13 | 36.22 | 50.92 |
| 2,3-Dimethylbutane | 2.40 | 12.02 | 13.51 | 8.18 | | | | | | |
| 2-Methylpentane | 81.13 | 26.48 | 29.65 | 17.87 | | | | | | |
| 3-Methylpentane | 1.69 | 10.83 | 12.16 | 7.90 | | | | | | |
| n-Hexane | 0 | 3.65 | 383 | 3.27 | | | | | | |
| Methylcyclopentane | 14.77 | 0.73 | 0.79 | 0.71 | | | | | | |
| Cyclohexane | 0 | 11.22 | 13.02 | 12.13 | | | | | | |
| Higher | 0 | 0.27 | 0.23 | 0.34 | | | | | | |
| Composition of Hexane Fraction, Weight Percent* | | | | | | | | | | |
| 2,2-Dimethylbutane | 0 | — | 31.18 | 57.66 | 41.63 | 64.71 | 45.23 | 58.75 | 42.71 | 59.82 |
| 2,3-Dimethylbutane | 2.82 | — | 16.72 | 9.93 | | | | | | |
| 2-Methylpentane | 95.2 | — | 34.50 | 20.61 | | | | | | |
| 3-Methylpentane | 1.98 | — | 14.15 | 8.53 | | | | | | |
| n-Hexane | 0 | — | 4.46 | 3.77 | | | | | | |
| C | 0.0005 | | | 0.00033 | | 0.0011 | | 0.0022 | | 0.003 |
| C/A | 0.001 | | | 0.00026 | | | | 0.0016 | | 0.002 |

| Batch Number | 10 | 11 | 12 | 13 | 14 | 15 | 16 | 17 | 18 |
|---|---|---|---|---|---|---|---|---|---|
| Batch Contact Time, hours | 7.0 | 16.3 | 7.1 | 16.2 | 7.2 | 64.0 | 6.6 | 17 | 4.4 |
| Total Time on Stream, hours | 168 | 184 | 192 | 208 | 216 | 280 | 288 | 301 | 308 |
| Composition of Hydrocarbon, Weight Percent* | | | | | | | | | |
| Propane | 0 | 0 | 0 | 0.03 | 0 | 0.23 | 0.01 | 0.06 | 0 |
| Isobutane | 0.21 | 0.51 | 0.30 | 0.61 | 0.37 | 2.97 | 0.60 | 1.42 | 0.54 |
| n-Butane | 0 | 0 | 0 | 0 | 0 | 0.02 | 0 | 0 | 0 |
| Isopentane | 0.06 | 0.15 | 0.09 | 0.18 | 0.11 | 1.12 | 0.25 | 0.48 | 0.19 |
| n-Pentane | 0 | 0 | 0 | 0 | 0 | 0.12 | 0.02 | 0.04 | 0 |
| 2,2-Dimethylbutane | 37.51 | 51.0 | 37.38 | 49.97 | 37.76 | 51.69 | 35.61 | 49.86 | 28.44 |
| 2,3-Dimethylbutane | | | | | | | | | |
| 2-Methylpentane | | | | | | | | | |
| 3-Methylpentane | | | | | | | | | |
| n-Hexane | | | | | | | | | |
| Methylcyclopentane | | | | | | | | | |

TABLE VI-continued

| | | | | | | | | | | |
|---|---|---|---|---|---|---|---|---|---|---|
| Cyclohexane | | | | | | | | | | |
| Higher | | | | | | | | | | |
| Composition of Hexane Fraction, Weight Percent* | | | | | | | | | | |
| 2,2-Dimethylbutane | | 44.32 | 59.94 | 44.28 | 59.33 | 44.36 | 64.22 | 42.63 | 60.12 | 33.92 |
| 2,3-Dimethylbutane | | | | | | | | | | |
| 2-Methylpentane | | | | | | | | | | |
| 3-Methylpentane | | | | | | | | | | |
| n-Hexane | | | | | | | | | | |
| C | | | 0.0055 | | 0.0068 | | 0.0095 | | 0.0165 | |
| C/A | | | 0.0035 | | 0.0046 | | | | 0.0103 | |
| Batch Number | 19 | 20 | 21 | 22 | 23 | 24 | 25 | 26 | 27 | 28 |
| Batch Contact Time, hours | 43 | 71 | 16.4 | 7.0 | 64.% | 6.8 | 16.6 | 7.1 | 40.5 | 4.8 |
| Total Time on Stream, hours | 352 | 360 | 376 | 383 | 449 | 456 | 472 | 480 | 520 | 525 |
| Composition of Hydrocarbon, Weight Percent* | | | | | | | | | | |
| Propane | 0.28 | 0.02 | 0.08 | 0.02 | 0.56 | 0.04 | 0.05 | 0.01 | 0.19 | 0.02 |
| Isobutane | 3.59 | 0.88 | 2.01 | 1.01 | 5.84 | 1.07 | 2.16 | 0.94 | 3.51 | 0.59 |
| n-Butane | 0.02 | 0 | 0 | 0 | 0.04 | 0 | 0 | 0 | 0.02 | 0 |
| Isopentane | 1.54 | 0.36 | 0.86 | 0.38 | 3.3 | 0.57 | 0.90 | 0.30 | 1.68 | 0.30 |
| n-Pentane | 0.17 | 0.03 | 0.07 | 0.02 | 0.39 | 0.04 | 0.07 | 0.02 | 0.18 | 0.01 |
| 2,2-Dimethylbutane | 51.4 | 35.84 | 49.47 | 35.6 | 47.49 | 28.2 | 44.17 | 27.36 | 51.33 | 16.61 |
| 2,3-Dimethylbutane | | | | | | | | | | |
| 2-Methylpentane | | | | | | | | | | |
| 3-Methylpentane | | | | | | | | | | |
| n-Hexane | | | | | | | | | | |
| Methylcyclopentane | | | | | | | | | | |
| Cyclohexane | | | | | | | | | | |
| Higher | | | | | | | | | | |
| Composition of Hexane Fraction, Weight Percent* | | | | | | | | | | |
| 2,2-Dimethylbutane | 64.74 | 43.0 | 60.3 | 42.8 | 63.79 | 34.01 | 54.04 | 32.87 | 65.68 | 19.77 |
| 2,3-Dimethylbutane | | | | | | | | | | |
| 2-Methylpentane | | | | | | | | | | |
| 3-Methylpentane | | | | | | | | | | |
| n-Hexane | | | | | | | | | | |
| C | 0.018 | | 0.0252 | | 0.0222 | | 0.0263 | | | |
| C/A | | | 0.0155 | | | | 0.0263 | | | |

*Where blank spaces occur values have not been tabulated.

EXAMPLE VI

This Example was carried out using the amounts set out in EXAMPLE I except that 16.35 milliliters (27.95 grams) of fluorosulfonic acid and 0.95 milliliters (0.95 grams) of hydrogen fluoride were employed and the temperature during the run was held at −6° C.

TABLE VII

| Batch Number | | 1 | 2 | 3 | 4 | 5 | 6 | 7 | 8 | 9 |
|---|---|---|---|---|---|---|---|---|---|---|
| Batch Contact Time, Hours | | 16.2 | 7.0 | 64.4 | 7.1 | 16.2 | 7.3 | 16.1 | 7.4 | 16 |
| Total Time on Stream, Hours | | 16.2 | 24.0 | 88 | 95 | 112 | 114 | 136 | 144 | 160 |
| Composition of Hydrocarbon, Weight Percent* | Feed | | | | | | | | | |
| Propane | 0 | 0 | 0 | 0.02 | 0 | 0.01 | 0 | 0 | 0 | 0 |
| Isobutane | 0 | 0.01 | 0.03 | 0.02 | 0.07 | 0.03 | 0.08 | 0.13 | 0.07 | 0.13 |
| n-Butane | 0 | 0 | 0 | 0 | 0 | 0 | 0 | 0 | 0 | 0 |
| Isopentane | 0 | 0.09 | 0.02 | 0.10 | 0.03 | 0.05 | 0.03 | 0.04 | 0.03 | 0.04 |
| n-Pentane | 0 | 0 | 0 | 0 | 0 | 0 | 0 | 0 | 0 | 0 |
| 2,2-Dimethylbutane | 0 | 2.19 | 7.25 | 58.65 | 38.68 | 52.3 | 41.31 | 52.82 | 41.17 | 52.93 |
| 2,3-Dimethylbutane | 2.4 | 16.14 | 18.8 | 6.87 | | | | | | |
| 2-Methylpentane | 87.13 | 58.17 | 41.25 | 14.41 | | | | | | |
| 3-Methylpentane | 1.69 | 23.02 | 16.94 | 6.05 | | | | | | |
| n-Hexane | 0 | 0.44 | 1.48 | 2.36 | | | | | | |
| Methylcyclopentane | 14.77 | 1.75 | 0.85 | 0.53 | | | | | | |
| Cyclohexane | 0.0 | 4.82 | 10.33 | 20.4 | | | | | | |
| Higher | 0.0 | 0.44 | 0.17 | 0.34 | | | | | | |
| Composition of Hexane Fraction, Weight Percent* | Feed | | | | | | | | | |
| 2,2-Dimethylbutane | 2.19 | 2.19 | 8.46 | 66.39 | 45.16 | 60.81 | 48.59 | 61.39 | 48.58 | 63 |
| 2,3-Dimethylbutane | 3.3 | 16.19 | 21.93 | 7.78 | | | | | | |
| 2-Methylpentane | 95.5 | 58.17 | 48.12 | 16.31 | | | | | | |
| 3-Methylpentane | 1.1 | 23.02 | 14.76 | 6.85 | | | | | | |
| n-Hexane | 0.1 | 0.44 | 1.73 | 2.67 | | | | | | |
| C | | | 0.00079 | | 0.0033 | | 0.00079 | | 0.00071 | | 0.00071 |
| C/A | | | 0.088 | | | | 0.00090 | | 0.00074 | | 0.00071 |
| Batch Number | | 10 | 11 | 12 | 13 | 14 | 15 | 16 | 17 | 18 |
| Batch Contact Time, Hours | | 8 | 16.3 | 7.3 | 64.1 | 6.73 | 16.2 | 7.3 | 16.1 | 6.95 |
| Total Time on Stream, Hours | | 168 | 189 | 192 | 257 | 263 | 280 | 288 | 304 | 311 |
| Composition of Hydrocarbon, Weight Percent* | | | | | | | | | | |
| Propane | | 0 | 0 | 0 | 0.06 | 0 | 0.02 | 0 | 0 | 0 |
| Isobutane | | 0.08 | 0.10 | 0.73 | 0.2 | 0.35 | 0.21 | 0.46 | 0.28 | |
| n-Butane | | 0.19 | | | | | | | | |
| | | 0 | 0 | 0 | 0 | 0 | 0 | 0 | 0 | 0 |
| Isopentane | | 0.03 | 0.06 | 0.04 | 0.2 | 0.06 | 0.11 | 0.07 | 0.15 | 0.11 |
| n-Pentane | | 0 | 0 | 0 | 0 | 0 | 0 | 0 | 0 | 0 |
| 2,2-Dimethylbutane | | 41.68 | 52.65 | 41.02 | 55.27 | 39.38 | 52.33 | 41.27 | 51.08 | 36.73 |
| 2,3-Dimethylbutane | | | | | | | | | | |
| 2-Methylpentane | | | | | | | | | | |

TABLE VII-continued

| | | | | | | | | | |
|---|---|---|---|---|---|---|---|---|---|
| 3-Methylpentane | | | | | | | | | |
| n-Hexane | | | | | | | | | |
| Methylcyclopentane | | | | | | | | | |
| Cyclohexane | | | | | | | | | |
| Higher | | | | | | | | | |
| Composition of Hexane Fraction, Weight Percent | | | | | | | | | |
| 2,2-Dimethylbutane | 49.0 | 61.52 | 48.31 | 65.24 | 46.68 | 61.31 | 48.56 | 60.33 | 44.06 |
| 2,3-Dimethylbutane | | | | | | | | | |
| 2-Methylpentane | | | | | | | | | |
| 3-Methylpentane | | | | | | | | | |
| n-Hexane | | | | | | | | | |
| C | | 0.00103 | | 0.00105 | | 0.0020 | | 0.00256 | |
| C/A | | 0.00106 | | 0.002 | | 0.0021 | | 0.00308 | |
| Batch Number | 19 | 20 | 21 | 22 | 23 | 24 | 25 | 26 | 27 |
| Batch Contact Time, Hours | 16.45 | 6.82 | 16.9 | 7.0 | 64.6 | 6.8 | 16.5 | 7.3 | 16.4 |
| Total Time on Stream, Hours | 328 | 335 | 352 | 355 | 424 | 431 | 448 | 456 | 472 |
| Composition of Hydrocarbon, Weight Percent* | | | | | | | | | |
| Propane | 0.04 | 0 | 0.04 | 0 | 0.3 | 0.02 | 0.07 | 0 | 0.07 |
| Isobutane | 0.73 | 0.38 | 0.86 | 0.54 | 3.40 | 0.81 | 1.46 | 6.76 | 1.64 |
| n-Butane | 0 | 0 | 0 | 0 | 0.02 | — | — | — | — |
| Isopentane | 0.22 | 0.14 | 0.28 | 0.19 | 1.45 | 0.57 | 0.50 | 0.28 | 0.62 |
| n-Pentane | 0.02 | 0 | 0.02 | 0 | 0.15 | 0.03 | 0.04 | 0.02 | 0.05 |
| 2,2-Dimethylbutane | 50.87 | 35.98 | 50.19 | 36.42 | 49.91 | 35.76 | 45.53 | 37.96 | 48.31 |
| 2,3-Dimethylbutane | | | | | | | | | |
| 2-Methylpentane | | | | | | | | | |
| 3-Methylpentane | | | | | | | | | |
| n-Hexane | | | | | | | | | |
| Methylcyclopentane | | | | | | | | | |
| Cyclohexane | | | | | | | | | |
| Higher | | | | | | | | | |
| Composition of Hexane Fraction, Weight Percent* | | | | | | | | | |
| 2,2-Dimethylbutane | 60.30 | 43.25 | 54.84 | 43.92 | 63.4 | 43.37 | 56.15 | 45.18 | 54.29 |
| 2,3-Dimethylbutane | | | | | | | | | |
| 2-Methylpentane | | | | | | | | | |
| 3-Methylpentane | | | | | | | | | |
| n-Hexane | | | | | | | | | |
| C | | 0.00415 | | 0.0048 | | 0.0057 | | 0.0085 | 0.0101 |
| C/A | | 0.0051 | | 0.0064 | | | | 0.0150 | 0.0138 |

*Where blank spaces occur values have not been tabulated.

EXAMPLE VII

This Example was carried out using the amounts set out in EXAMPLE 1 except that 15.6 milliliters (26.8 grams) of fluorosulfonic acid and 2.9 milliliters (2.9 grams) of hydrogen fluoride were employed and the temperature during the run was held at −6° C.

TABLE VIII

| Batch Number | | 1 | 2 | 3 | 4 | 5 | 6 | 7 | 8 | 9 | 10 |
|---|---|---|---|---|---|---|---|---|---|---|---|
| Batch Contact Time, hours | | 18.2 | 6.8 | 16.5 | 6.9 | 64.2 | 6.7 | 16.1 | 7.0 | 16.2 | 7.6 |
| Total Time on Stream, hours | | 18.0 | 26 | 42 | 49 | 114 | 122 | 138 | 146 | 162 | 170 |
| Composition of Hydrocarbon, Weight Percent* | Feed | | | | | | | | | | |
| Propane | 0 | 0.01 | 0 | 0 | 0 | 0.04 | 0 | 0.02 | 0 | 0.01 | 0 |
| Isobutane | 0 | 0.01 | 0.05 | 0.04 | | 0.42 | 0.17 | 0.24 | 0.12 | 0.21 | 0.12 |
| n-Butane | 0 | 0.08 | 0 | 0 | | 0 | 0 | 0 | 0 | 0.02 | 0 |
| Isopentane | 0 | 0.17 | 0.06 | 0.04 | | 0.15 | 0.07 | 0.08 | 0.05 | 0.08 | 0.05 |
| n-Pentane | 0 | 0 | 0 | 0 | | 0 | 0 | 0 | 0 | 0 | 0 |
| 2,2-Dimethylbutane | 0 | 56.69 | 38.24 | 54.21 | | 53.17 | 44.0 | 49.92 | 38.86 | 49.40 | 41.64 |
| 2,3-Dimethylbutane | 2.4 | | | | | | | | | | |
| 2-Methylpentane | 87.13 | | | | | | | | | | |
| 3-Methylpentane | 1.69 | | | | | | | | | | |
| n-Hexane | 0 | | | | | | | | | | |
| Methylcyclopentane | 14.77 | | | | | | | | | | |
| Cyclohexane | 0 | | | | | | | | | | |
| Higher | 0 | | | | | | | | | | |
| Composition of Hexane Fraction, Weight Percent* | | | | | | | | | | | |
| 2,2-Dimethylbutane | 0.0 | 61.25 | 49.11 | 61.62 | | 61.58 | 51.03 | 58.80 | 46.09 | 58.44 | 49.36 |
| 2,3-Dimethylbutane | 3.3 | | | | | | | | | | |
| 2-Methylpentane | 95.5 | | | | | | | | | | |
| 3-Methylpentane | 1.1 | | | | | | | | | | |
| n-Hexane | 0.1 | | | | | | | | | | |
| C | | 0.0016 | 0.0011 | 0.00033 | | 0.00064 | | 0.0015 | | 0.0013 | |
| C/A | | 0.0020 | 0.0015 | 0.00033 | | | | 0.0020 | | 0.0019 | |
| Batch Number | | 11 | 12 | 13 | 14 | 15 | 16 | 17 | 18 | 19 | 20 |
| Batch Contact Time, hours | | 15.9 | 6.9 | 16.1 | 7.1 | 64.1 | 7.5 | 15.9 | 3.3 | 16.2 | 7.0 |
| Total Time on Stream, hours | | 186 | 193 | 205 | 217 | 282 | 289 | 305 | 313 | 330 | 337 |
| Composition of Hydrocarbon, Weight Percent* | | | | | | | | | | | |
| Propane | | 0 | 0 | 0.2 | 0 | 0.01 | 0.01 | 0 | 0 | 0.03 | 0.01 |
| Isobutane | | 0.22 | 0.14 | 0.30 | 0.17 | 1.18 | 0.29 | 0.29 | 0.21 | 0.50 | 0.32 |
| n-Butane | | 0 | 0 | 0 | 0 | 0 | 0 | 0 | 0 | 0 | 0 |
| Isopentane | | 0.07 | 0.05 | 0.1 | 0.07 | 0.36 | 0.12 | 0.12 | 0.09 | 0.18 | 0.13 |
| n-Pentane | | 0 | 0 | 0 | 0 | 0.03 | 0.01 | 0.04 | 0 | 0.02 | 0.01 |
| 2,2-Dimethylbutane | | 50.83 | 43.11 | 50.70 | 41.32 | 53.42 | 42.5 | 50.2 | 27.8 | 53.10 | 43.13 |

TABLE VIII-continued

| | | | | | | | | | | | |
|---|---|---|---|---|---|---|---|---|---|---|---|
| 2,3-Dimethylbutane | | | | | | | | | | | |
| 2-Methylpentane | | | | | | | | | | | |
| 3-Methylpentane | | | | | | | | | | | |
| n-Hexane | | | | | | | | | | | |
| Methylcyclopentane | | | | | | | | | | | |
| Cyclohexane | | | | | | | | | | | |
| Higher | | | | | | | | | | | |
| Composition of Hexane Fraction, Weight Percent* | | | | | | | | | | | |
| 2,2-Dimethylbutane | | 60.29 | 50.73 | 59.93 | | 49.35 | 63.41 | 50.73 | 59.06 | 33.26 | 62.00 | 48.37 |
| 2,3-Dimethylbutane | | | | | | | | | | | | |
| 2-Methylpentane | | | | | | | | | | | | |
| 3-Methylpentane | | | | | | | | | | | | |
| n-Hexane | | | | | | | | | | | | |
| C | | 0.0012 | | 0.0018 | | 0.0018 | | 0.0019 | | 0.0037 | |
| C/A | | 0.0015 | | 0.0022 | | | | 0.0026 | | 0.0028 | |
| Batch Number | 25 | 30 | 35 | 40 | 45 | 50 | 55 | 60 | 65 | 70 | 73 |
| Batch Contact Time, hours | 64.1 | 7.3 | 64.3 | 7.2 | 65 | 7.2 | 43.9 | 16.3 | 7.0 | 7.2 | 16.3 |
| Total Time on Stream, hours | 450 | 515 | 628 | 683 | 745 | 851 | 893 | 1012 | 1067 | 1162 | 1203 |
| Composition of Hydrocarbon, Weight Percent* | | | | | | | | | | | |
| Propane | 0.23 | 0 | 0.33 | 0 | 0.33 | 0.02 | 0.30 | 0.09 | 0.03 | 0.02 | 0.08 |
| Isobutane | 2.71 | 0.59 | 3.77 | 0.81 | 3.71 | 0.94 | 3.62 | 1.83 | 1.03 | 1.00 | 2.10 |
| n-Butane | 0 | 0 | 0.03 | 0 | 0.02 | 0 | 0.02 | 0 | 0 | 0 | 0 |
| Isopentane | 1.23 | 0.40 | 2.14 | 0.38 | 2.03 | 0.41 | 1.85 | 0.81 | 0.50 | 0.47 | 1.01 |
| n-Pentane | 0.13 | 0 | 0.25 | 0.03 | 0.24 | 0.04 | 0.22 | 0.09 | 0.04 | 0.04 | 0.10 |
| 2,2-Dimethylbutane | 49.56 | 36.68 | 47.07 | 36.61 | 49.89 | 37.67 | 49.72 | 49.98 | 36.64 | 36.31 | 48.39 |
| 2,3-Dimethylbutane | | | | | | | | | | | |
| 2-Methylpentane | | | | | | | | | | | |
| 3-Methylpentane | | | | | | | | | | | |
| n-Hexane | | | | | | | | | | | |
| Methylcyclopentane | | | | | | | | | | | |
| Cyclohexane | | | | | | | | | | | |
| Higher | | | | | | | | | | | |
| Composition of Hexane Fraction, Weight Percent* | | | | | | | | | | | |
| 2,2-Dimethylbutane | 63.62 | 43.64 | 65.04 | 44.41 | 64.94 | 45.59 | 64.75 | 61.70 | 49.21 | 43.74 | |
| 2,3-Dimethylbutane | | | | | | | | | | | |
| 2-Methylpentane | | | | | | | | | | | |
| 3-Methylpentane | | | | | | | | | | | |
| n-Hexane | | | | | | | | | | | |
| C | 0.0046 | | 0.0071 | | 0.007 | | 0.0095 | 0.0118 | | 0.0137 | |
| C/A | | | | | | | | 0.0117 | | 0.0191 | |

*Where blank spaces occur the values have not been tabulated.

EXAMPLE VIII

This Example is a comparative EXAMPLE and uses 40 milliliters (40 grams) of hydrogen fluoride, 13 milliliters (39 grams) of antimony pentafluoride and 175 milliliters of a 2-methylpentane-methylcyclopentane mixture. The run temperature was −6° C.

TABLE IX

| Batch Number | | 1 | 2 | 3 | 4 | 5 | 6 | 7 | 8 | 9 | 10 | 11 |
|---|---|---|---|---|---|---|---|---|---|---|---|---|
| Batch Contact Time, hours | | 15.7 | 6.8 | 41.9 | 22.42 | 7.33 | 16.7 | 7.08 | 16.33 | 7.0 | 16.37 | 7.25 |
| Total Time on Stream, hours | | 15.7 | 23.0 | 65.1 | 87.8 | 95.4 | 112 | 114 | 136 | 143 | 160 | 167 |
| Composition of Hydrocarbon, Weight Percent | Feed | | | | | | | | | | | |
| Propane | 0 | 0.02 | 0 | 0.02 | 0.01 | 0 | 0 | 0 | 0.02 | 0 | 0.03 | 0.02 |
| Isobutane | 0 | 0.08 | 0.05 | 0.21 | 0.15 | 0.08 | 0.17 | 0.11 | 0.25 | 0.15 | 0.44 | 0.30 |
| n-Butane | 0 | 0 | 0 | 0.01 | 0 | 0 | 0.0 | 0.0 | 0.0 | 0.0 | 0 | 0 |
| Isopentane | 0 | 0.04 | 0.03 | 0.09 | 0.06 | 0.03 | 0.06 | 0.04 | 0.09 | 0.05 | 0.18 | 0.13 |
| n-Pentane | 0 | 0 | 0 | 0.01 | 0 | 0 | 0 | 0.0 | 0.01 | 0.0 | 0.02 | 0.01 |
| 2,2-Dimethylbutane | 0 | 39.9 | 27.58 | 56.26 | 50.95 | 31.88 | 46.28 | 32.36 | 48.51 | 31.97 | 48.0 | 35.64 |
| 2,3-Dimethylbutane | 2.4 | | | | | | | | | | | |
| 2-Methylpentane | 81.13 | | | | | | | | | | | |
| 3-Methylpentane | 1.69 | | | | | | | | | | | |
| n-Hexane | 0 | | | | | | | | | | | |
| Methylcyclopentane | 14.77 | | | | | | | | | | | |
| Cyclohexane | 0 | | | | | | | | | | | |
| Higher | 0 | Composition of Hexane | | | | | | | | | | |
| Fraction, Weight Percent | | | | | | | | | | | | |
| 2,2-Dimethylbutane | 0.0 | 44.49 | 31.95 | 64.24 | 54.35 | 37.92 | 53.89 | 37.94 | 56.35 | 37.60 | 56.25 | |
| 2,3-Dimethylbutane | 2.82 | | | | | | | | | | | |
| 2-Methylpentane | 95.2 | | | | | | | | | | | |
| 3-Methylpentane | 1.98 | | | | | | | | | | | |
| n-Hexane | 0 | | | | | | | | | | | |
| A | | 0.0016 | 0.0016 | 0.0011 | 0.0013 | | 0.0019 | | 0.0031 | | 0.0055 | 0.0085 |
| C/A | | 0.0024 | 0.0018 | | 0.0012 | | 0.0019 | | 0.0026 | | 0.0047 | 0.0067 |
| Batch Number | | 12 | 13 | 14 | 15 | 16 | 17 | 18 | 19 | 20 | 21 | 22 |
| Batch Contact Time, hours | | 16.1 | 7.2 | 41.2 | 22.8 | 7.1 | 16.6 | 6.7 | 16.1 | 7.0 | 16.2 | 34.5 |
| Total Time on Stream, hours | | 184 | 191 | 233 | 256 | 263 | 280 | 287 | 304 | 311 | 327 | 375 |
| Composition of Hydrocarbon, Weight Percent | | | | | | | | | | | | |
| Propane | | 0.06 | 0.03 | 0.16 | 0.07 | 0.02 | 0.08 | 0.06 | 0.12 | 0.06 | 0.12 | 0.20 |

TABLE IX-continued

| | | | | | | | | | | | |
|---|---|---|---|---|---|---|---|---|---|---|---|
| Isobutane | 0.73 | 0.40 | 1.55 | 0.92 | 0.38 | 1.03 | 1.18 | 2.10 | 1.55 | 2.27 | 2.60 |
| n-Butane | 0 | 0 | 0.02 | 0 | 0.05 | 0 | 0.01 | 0.02 | 0.01 | 0.02 | 0.02 |
| Isopentane | 0.34 | 0.18 | 0.82 | 0.44 | 0.21 | 0.56 | 0.72 | 1.47 | 1.05 | 1.99 | 1.69 |
| n-Pentane | 0.04 | 0.02 | 0.10 | 0.04 | 0 | 0.05 | 0.05 | 0.15 | 0.07 | 0.15 | 0.19 |
| 2,2-Dimethylbutane | 48.3 | 33.68 | 52.17 | 50.31 | 28.52 | 42.94 | 27.65 | 42.31 | 26.61 | 43.30 | 49.03 |
| 2,3-Dimethylbutane | | | | | | | | | | | |
| 2-Methylpentane | | | | | | | | | | | |
| 3-Methylpentane | | | | | | | | | | | |
| n-Hexane | | | | | | | | | | | |
| Methylcyclopentane | | | | | | | | | | | |
| Cyclohexane | | | | | | | | | | | |
| Higher | | | | | | | | | | | |
| Composition of Hexane Fraction, Weight Percent | | | | | | | | | | | |
| 2,2-Dimethylbutane | 56.83 | 39.77 | 63.15 | 59.54 | 33.87 | 51.19 | 33.27 | 51.62 | 32.26 | 52.83 | |
| 2,3-Dimethylbutane | | | | | | | | | | | |
| 2-Methylpentane | | | | | | | | | | | |
| 3-Methylpentane | | | | | | | | | | | |
| n-Hexane | | | | | | | | | | | |
| A | 0.0098 | 0.0018 | 0.0088 | 0.0088 | | 0.0140 | 0.0408 | | 0.0532 | | 0.0064 |
| C/A | 0.0080 | 0.0100 | | 0.0081 | | 0.0163 | 0.0430 | | 0.0615 | | 0.0221 |

What is claimed is:

1. A catalyst composition comprising fluorosulfonic acid and antimony pentafluoride in a volume ratio of antimony pentafluoride to fluorosulfonic acid of about 0.1 to about 3 and about two to about twenty weight percent of hydrogen fluoride based upon the weight of fluorosulfonic acid.

2. The composition of claim 1 wherein said weight percent is about three to about fifteen.

3. The composition of claim 1 wherein said weight percent is about five to about ten.

4. The composition of claim 1 wherein said volume ratio is about 0.4 to about 1.6.

5. The composition of claim 2 wherein said volume ratio is about 0.4 to about 1.6.

6. The composition of claim 3 wherein said volume ratio is about 0.4 to about 1.6.

7. A process for upgrading the octane rating of pentanes, hexanes or mixtures thereof which comprises contacting under isomerizing conditions said pentanes, hexanes or mixtures thereof, an inhibitor to prevent runaway cracking and a composition comprising:
   (1) fluorosulfonic acid and antimony pentafluoride in a volume ratio of antimony pentafluoride to fluorosulfonic acid of about 0.1 to about 3; and
   (2) about two to about twenty weight percent of hydrogen fluoride based upon the weight of fluorosulfonic acid.

8. The process of claim 7 wherein said weight percent is about three to about fifteen 9. The process of claim 7 wherein said weight percent is about five to about ten.

10. The process of claim 7 wherein said volume ratio is about 0.4 to about 1.6.

11. The process of claim 8 wherein said volume ratio is about 0.4 to about 1.6.

12. The process of claim 9 wherein said volume ratio is about 0.4 to about 1.6.

13. A continuous process for treating a stream of dearomatized pentanes, hexanes or a mixture thereof in the presence of about two to about thirty weight percent of an inhibitor to prevent runaway cracking comprising:
   (a) intimately contacting under isomerising conditions said stream with a catalyst composition consisting essentially of
      (1) fluorosulfonic acid and antimony pentafluoride in a volume ratio of antimony pentafuoride to fluorosulfonic acid of about one-tenth to about three, and
      (2) about two to about twenty weight percent of hydrogen fluoride based upon the weight of fluorosulfonic acid;
   (b) thereafter separating the product of (a) into a first hydrocarbon stream and a first catalyst stream;
   (c) returning a major portion of said first catalyst stream to (a) and a minor portion to a catalyst regeneration zone;
   (d) intimately contacting under isomerizing conditions said first hydrocarbon stream with additional said catalyst composition at a lower temperature than that used in (a);
   (e) thereafter separating the product of (d) into a second hydrocarbon stream and a second catalyst stream;
   (f) returning a major portion of said second catalyst stream to (d) and a minor portion to (a); and
   (g) adding make-up of said catalyst composition to and removing isomerized hydrocarbon product from the last contacting-separation step.

14. The process of claim 13 wherein said weight percent is about three to about fifteen and said volume ratio is about four-tenths to about one and six-tenths.

* * * * *

UNITED STATES PATENT OFFICE
CERTIFICATE OF CORRECTION

Patent No. 4,144,282     Dated March 13, 1979

Inventor(s) McCaulay, David A.

It is certified that error appears in the above-identified patent and that said Letters Patent are hereby corrected as shown below:

Title Page - "Reed F. Filey" - should be "Reed F. Riley"

Co. 4, line 64 - after equation, insert "where K is the rate constant"

Table I - under Col. 15, 3rd entry - "0.21" should be "0.19"

Table I - Insert omitted footnote - "*Milliliters neohexane per milliliter of antimony pentafluoride Table II - Line $k_{-5^\circ}$ Col. 25 - "0.017" should be "0.107"

Table II - Line $k_{-5^\circ}$, Col. 40 - "0.013" should be "0.103"

Table IV - Line A*** - All columns should be shifted one column to the right.

Table VII - Line 9 - Remove "0" after Isopentane. Also, shift all columns one column to the right.

Table VII - Cols. 11-17 for Isobutane should be shifted one column to the right, insert 0.19 in Col. 11, delete 0.19 from Col. 10.

UNITED STATES PATENT OFFICE
CERTIFICATE OF CORRECTION

Patent No. 4,144,282           Dated   March 13, 1979

Inventor(s) McCaulay, David A.

It is certified that error appears in the above-identified patent and that said Letters Patent are hereby corrected as shown below:

Table VIII - Shift "87.13" after 2-Methylpentane to "Feed" column.

Table IX - "Composition of Hexane" should be shifted from Col. 1 in center of table to extreme left.

Signed and Sealed this

Thirteenth Day of November 1979

[SEAL]

Attest:

RUTH C. MASON
Attesting Officer

LUTRELLE F. PARKER
Acting Commissioner of Patents and Trademarks